United States Patent [19]
Saxinger

[11] Patent Number: 6,031,074
[45] Date of Patent: *Feb. 29, 2000

[54] AUTOMATED PEPTIDE DESIGN AND SYNTHESIS

[75] Inventor: Carl Saxinger, Bethesda, Md.

[73] Assignee: National Institutes of Health, Rockville, Md.

[ * ] Notice: This patent is subject to a terminal disclaimer.

[21] Appl. No.: 07/398,458

[22] Filed: Aug. 25, 1989

[51] Int. Cl.$^7$ ............................. A61K 38/00; C07K 5/00; C07K 7/00

[52] U.S. Cl. ............................................ 530/334; 530/333

[58] Field of Search ............................. 525/240; 530/334, 530/341, 333

[56] References Cited

U.S. PATENT DOCUMENTS

| | | | |
|---|---|---|---|
| 3,725,380 | 4/1973 | Mönig et al. | 260/112.5 R |
| 3,944,538 | 3/1976 | Bodanszky | 260/112.5 |
| 3,953,415 | 4/1976 | Kisfaludy et al. | 260/112.5 R |
| 4,192,798 | 3/1980 | Verlander et al. | 260/112.5 R |
| 4,330,440 | 5/1982 | Ayers et al. | 525/54.31 |
| 4,436,874 | 3/1984 | Asipsi et al. | 525/327.1 |
| 4,631,211 | 12/1986 | Houghten | 428/35 |
| 4,812,512 | 3/1989 | Buendia et al. | 525/54.11 |

OTHER PUBLICATIONS

Geysen et al., PNAS USA vol. 81 pp. 3998–4002 (Jul. 1984).

Melby, Macromolecules, vol 11, No. 1 (Jan./Feb. 1978). pp. 50–56.

Proc. Natl. Acad. Sci. USA, vol. 82, pp. 5131–5135, Aug. 1985 Immunology, Richard A. Houghten.

Angewandte Chemie, International English Edition, vol.24, No.10, pp. 799–892, Oct. 1985.

Journal of American Chem.Soc., vol. 89, No. 1, pp.183–184, Jan. 1967.

Science, vol. 150, pp. 178–185, Oct. 1965.

Merrifield R.B. 24 Angen Chemie No. 10 (1985) pp. 799–810.

Daniels et al., 30 Tetrahedron Letters No. 33 pp. 4345–4348 (Sep. 6, 1989).

Beauchamp et al. 131 Analytical Biochem. 25–33 (1983).

Arshady et al. J. C. S . Perkins Tran I 529–537 (1981).

Melby CA 1218775 vol. 88 (1978).

Ryzanteev CA 72818 F vol. 78 (1973).

Stewart and Young, "Solid Phase Peptide Synthesis" (2nd ed) (Pierce Chemical Co 1984) 1–7.

Houghten, PNAS USA, vol. 82 pp. 5131–5135 (Aug. 1985).

Geysen et al, PNAS USA vol. 81 pp. 3998–4002 (Jul. 1984).

Ryzanteev et al CA 72818F vol. 78 (1973).

Melby Macromolecules vol. 11 No. 1 (Jan./Feb. 1978).

*Primary Examiner*—Avis M. Davenport

[57] ABSTRACT

An automated peptide design and synthesis method is provided, wherein peptides are synthesized on interior, inward facing surfaces of reservoirs formed in a solvent resistant substrate. Novel substrates, as well as novel solutions for storing protected carboxyl terminal amino acids, are also provided.

7 Claims, 4 Drawing Sheets

FIG. 3

AUTOMATED PEPTIDE DESIGN AND SYNTHESIS

BACKGROUND OF THE INVENTION

Solid-phase chemical peptide synthesis methods have been known in the art since the early 1960's (Merrifield, R. B., *J. Am. Chem. Soc.*, 85, 2149–2154 (1963) (See also Stewart, J. M. and Young, J. D., *Solid Phase Peptide Synthesis*, 2 ed., Pierce Chemical Co., Rockford, Ill., pp. 11–12)) and have recently been employed in commercially available laboratory peptide design and synthesis kits (Cambridge Research Biochemicals). Such commercially available laboratory kits have generally utilized the teachings of H. M. Geysen et al, *Proc. Natl. Acad. Sci., USA*, 81, 3998 (1984) and provide for synthesizing peptides upon the tips of a multitude of "rods" or "pins" all of which are connected to a single plate. When such a system is utilized, a plate of rods or pins is inverted and inserted into a second plate of corresponding wells or reservoirs, which contain solutions for attaching or anchoring an appropriate amino acid to the pin's or rod's tips. By repeating such a process step, i.e., inverting and inserting the rod's and pin's tips into appropriate solutions, amino acids are built into desired peptides.

While the above rod or pin system can be extremely efficient in preparing peptides (Geysen, H. M. et al, *J. Immunol. Methods*, 102, 259–274 (1987)) it cannot be easily automated, since the plate which holds the rods or pins must be repeatedly inverted and inserted into wells or reservoirs of desired solutions. The automation of such a process step (inversion and insertion) would not only be considered difficult, but is also so specialized as to preclude the use of general laboratory equipment, to perform such a step. It is for such reasons that the prior art method of peptide synthesis on rod or pin tips is performed manually. Manual peptide synthesis, of course, requires that lab personnel be present throughout peptide synthesis, and as such, the prior art teachings of protein synthesis utilizing rod or pin technology burdens laboratories by requiring that personnel be present when peptide synthesis is to be performed.

SUMMARY OF THE INVENTION

A first object of the present invention was to remove the necessity for an inversion and insertion step in a laboratory peptide synthesis method, such a step being required with known "rod" or "pin" peptide synthesis technology and such a step being considered a hindrance to the automation of a laboratory peptide synthesis method.

A second object of the present invention was to provide for an automated peptide synthesis method which could be performed on a general, readily available, laboratory work station, and thus not force laboratories to spend large capital sums for specialized laboratory equipment, capable of performing only a single specialized task, i.e., automated peptide synthesis.

A third object of the present invention was to provide for stable amino acid solutions capable of being prepared in advance and stored for prolonged periods of time prior to utilization in automated peptide synthesis methods; thus further alleviating burdens on laboratory personnel, by removing any need for preparing such solutions immediately prior to protein synthesis.

A fourth object of the present invention was to provide an automated method applicable to the automation of a Biomek 1000™ general laboratory workstation so that the same could be utilized to perform an automated peptide synthesis.

In view of the above objects, I provide for the following:

1. A solvent resistant substrate having one or more reservoirs therein, wherein each of said reservoirs opens on a single surface of said substrate, and wherein at least a portion of an interior, inward facing, surface of at least one of the reservoirs in said substrate has been activated for the anchoring of a carboxyl terminal amino acid thereto.

2. The solvent resistant substrate recited in paragraph (1), wherein the substrate is selected from one of the following: a polyolefin substrate, a glass substrate, a DELRIN substrate, a Costar TPX substrate.

3. The solvent resistant substrate as recited in paragraph (1), wherein said substrate is in a microtiter format.

4. The solvent resistant substrate recited in paragraph (1), wherein the substrate is a polyolefinic substrate, which has been activated by reacting sequentially with: (1) nitric acid at room temperature or at an elevated temperature; (2) with a carbonyldiimidazole; and (3) with a polyamine.

5. A process for the solid phase chemical synthesis of peptides, which process comprises the steps of:
   (a) obtaining a solvent resistant substrate having one or more reservoirs therein, wherein each of said reservoirs opens on a single surface of said substrate, and wherein at least a portion of an interior, inward facing, surface of one or more reservoirs therein has been activated for the anchoring of a protected carboxyl terminal amino acid thereto;
   (b) anchoring a first protected carboxyl terminal amino acid to said activated sites on said interior, inwardly facing, surfaces of said reservoirs;
   (c) deprotecting the protected carboxyl terminal amino acid at the $\alpha$-amino position of said amino acid;
   (d) connecting a second protected carboxyl terminal amino acid to the amine formed in step (c); and
   (e) sequentially repeating steps (c) and (d).

6. The process as recited in paragraph (5), wherein said solvent resistant substrate is the solvent resistant substrate recited in paragraph (4).

7. The process as recited in paragraph (5), wherein said solvent resistant substrate is selected from the following: a polyolefinic substrate, a glass substrate, a DELRIN substrate or a COSTAR TPX substrate.

8. The process as recited in paragraph (5), wherein said first or second protected carboxyl terminal amino acid is an amino acid, having its $\alpha$-amino group blocked by a protecting group selected from: 9-fluorenyl-methoxy-carbonyl, 2-(4-biphenylyl)-propyl(2)oxycarbonyl, 2-phenyl-propyl (2)-oxycarbonyl or t-butoxycarbonyl.

9. The process as recited in paragraph (5), wherein said protected carboxyl terminal amino acid has its $\alpha$-amino group blocked by a 9-fluorenyl-methoxycarbonyl protecting group.

10. The process as recited in paragraph (5), wherein said solvent resistant substrate is in a microtiter format, and said process is automated.

11. A method for automating the process, as recited in paragraph (5), on a Beckman Biomek 1000™ laboratory workstation.

12. A stable solution for storing protected amino acid intermediates, at a temperature of about at most $-20°$ C., which solution comprises:
   (a) a protected carboxyl terminal amino acid, preferably in the amount of 0.1 M to 1.0 M, more preferably in an amount of 0.2 M to 0.5 M; and
   (b) hydroxybenzotriazole, pentafluorophenol, or any other weakly acidic compound which can form a subsequent active ester with said amino acid, preferably in the amount of 0.1 M to 1.0 M, more preferably in an amount of 0.2 M to 0.5 M;

in a solvent having hydrogen bond donor and/or accepting properties, in which derivative amino acids are freely soluble and stable, and preferably which can solvate long peptide product chains.

13. A process for forming an activated amino acid intermediate, for immediate use (within about 24 hr.) in the manual or automated synthesis of peptides, which process comprises the steps of:

Step (a) storing for up to more than 3 months, at a temperature of about at most −20° C., a solution which comprises:

(1) a protected carboxyl terminal amino acid; and (2) a weakly acidic compound which can form a subsequent active ester with said amino acid (e.g., hydroxybenzotriazole or pentaflurophenyl);

in a suitable solvent having hydrogen bond donor and/or accepting properties, in which derivative amino acids are freely soluble and stable, and preferably which can solvate long peptide product chains; and Step (b) adding a condensation agent, preferably in an equimolar amount or in a 10–30% excess thereof, based on the amount of amino acid present, to at least a portion of said solution from step (a), within about 24 hours of beginning a manual or automated peptide synthesis utilizing said portion of said solution.

In order to remove any ambiguity which may exist as to the meaning of certain terms utilized herein, the following glossary of terms is provided. The same glossary, however, should not be considered to unduly limit the present invention, inasmuch as many of the terms utilized may have additional meanings or equivalents, readily understood by those skilled in the art.

The term "solvent resistant substrate" as used herein, means a substrate which is insoluble and inert to solvents commonly utilized in the synthesis of peptides; and which also allows for the eventual anchoring or attachment of a peptide thereto. Such substrates would include, for example, polyolefins such as polyethylene and polypropylene, glass, DELRIN (a linear polyoxymethylene-type acetyl resin), and Costar TPX (polymethyl-pentene). If there exist a doubt as to whether or not a particular substrate is acceptable to utilize herein, it should be at least insoluble and inert to the following solvents, which are normally used in peptide synthesis: dimethylformamide, methylene chloride and N-methyl-2-pyrrolidone and trifluoroacetic acid, and yet still be capable of being activated for the attachment of a peptide thereto. Examples of substrates excluded herefrom include, for example, polystyrene, polyvinyl chloride and TEFLON.

The term "reservoir" as used herein means an indentation, impression, cavity, sunken area or the like, in a solvent resistant substrate, wherein the indentation, etc., is capable of receiving and holding an appropriate quantity of a desired solution. The term is also meant to include those reservoirs having a portion of their inward surface as a filter type surface, for example, a bottom surface could be a filter through which liquids could be removed when desired. The term is also meant to include substrates having the configuration of a tube, capable of holding a volume of solution.

The term "interior, inward facing, surface" as utilized herein means surfaces of a reservoir, which come in contact with solutions placed in reservoirs, e.g., sidewalls, bottom, etc.

The term "protected carboxyl terminal amino acid" as utilized herein, means an amino acid selected from glycine, alanine, valine, isoleucine, leucine, serine, threonine, proline, aspartic acid, glutamic acid, lysine, arginine, asparagine, glutamine, cysteine, methionine, tryptophan, phenylalanine, tyrosine, or histidine, wherein the α-amino groups of the same amino acids have been blocked by a suitable protecting group selected from 9-fluorenyl-methoxycarbonyl, 2-phenyl-propyl (2) oxycarbonyl t-butoxycarbonyl, or the like, and wherein side chain functional groups on the amino acids are blocked with protecting groups such as t-butyl trityl, and BOC-based derivatives.

The term "protected carboxyl terminal amino acid" means protected carboxyl terminal amino acids, as defined herein, but also having left-hand chirality.

The term "polyolefin" as used herein means polyethylene, polypropylene and the like.

The term "TEFLON" as used herein is a trademarked name for polytetrafluoroethylene.

The term "DELRIN" as used herein, is a trademarked name for a linear polyoxymethylene-type acetyl resin, made by the copolymerization of formaldehyde, the same having a high strength and solvent resistance; mp 180° C.

The term "Costar TPX" as used herein, is a trademarked name for (polymethylpentene).

The term "elevated temperature" as used herein, means a temperature of about 90–100° C., more or less, at which carboxyl groups can be generated on a solvent resistant substrate when utilizing nitric acid or the like to oxidize at least a portion of interior, inward facing surfaces of reservoirs contained in the substrate.

The term "polyamine" as utilized herein, means an organic molecule having 2 or more amine groups thereon. Examples of such compounds include polyethyleneimine, polypropyleneimine, and the like.

The term "microtiter format" as used herein means multiwell microtiter plates, breakaway microtiter wells, strip microtiter wells, and test tube racks containing test tubes or cryovials.

The term "condensing agent" as used herein means a compound capable of activating carboxyl groups on amino acids so that the hydroxyl substituent of the carboxyl moiety of the amino acid is displaced and a carboxylic acid ester formed via a condensation reaction. Suitable condensation agents include cyanamide and associated derivatives thereof (e.g., cyclohexylcarbodiimide) as well as Castro's reagent, or the like.

The term "active ester intermediate" as used herein means the amino acid carboxyl esters formed with HOBT, pentafluorophenyl or the like (e.g., other weakly acetic compounds which can form a subsequent "active ester intermediate" with an amino acid).

The term "tertiary amine" as used herein means diisopropylethylamine, triethylamine, trimethylamine and the like.

The term "carbonyldiimidazole" as used herein means N,N'-carbonyldiimidazole and associated derivatives thereof which can react with carboxylic acid groups formed on substrates to form an acyl imidazole group on the substrates, which in turn can react with a polyamine to form an attachment site for a protected carboxyl terminal amino acid.

The following is a list of abbreviations which are used herein to aid those desiring to practice the present invention: N-methyl-2-pyrrolidone, NMP; hydroxybenzotriazole; dimethylformamide, DMF; dicyclohexylcarbodiimide, DCC; trifluoroacetic acid, TFA; 4-hydroxymethylphenoxy acetic acid, ALH; 4-hydroxymethyl-3-methoxyphenoxy acetic acid, HALH; 4-hydroxymethylbenzoic acid, BLH; 9-fluoroenyl-methoxycarbonyl, FMOC.

BRIEF DESCRIPTION OF THE DRAWINGS

The present invention will become more fully understood from the detailed description given below, and the accompanying drawings which are given by way of illustration only and are not intended to limit the present invention, and wherein.

The above-mentioned drawings 1, 2A and 2B will be described in detail in the following detailed description.

DETAILED DESCRIPTION OF THE INVENTION

Procedures are disclosed herein for both the manual and automated design and synthesis of peptides of any defined sequence of length, wherein the peptides produced are attached (or anchored) to previously activated, interior inward facing surfaces of reservoirs, which reservoirs are formed in solvent resistant substrates. Several preferred embodiments of the present invention exist, most principle of these, however, may be the use of solvent resistant substrates which utilize a "microtiter format". In such an instance, the substrate has multiple reservoirs therein, with at least a portion of inward facing reservoir surfaces, suitable for the attachment of peptides thereto.

Even though, the term "microtiter format" is used herein for discussing a preferred embodiment for solvent resistant substrates of the present invention, this is not meant to lessen the general applicability of procedures disclosed herein, to suitable substrates having other "formats" than a "microtiter format". This is mentioned, because the procedures disclosed herein are as applicable to building a peptide in, for example, a single "test tube" made of a suitable material, as they are to building distinct and different peptides in each well of a suitable "solvent resistant" microtiter plate substrate having multiple wells therein. It is also noted that suitable substrates can also have a tube like configuration wherein peptides are attached to the inward surfaces of the tube like configuration. Such a configuration would of course allow for the synthesis of peptide by pumping appropriate solutions through the tubing. It is also noted that a suitable substrate might have a portion thereof being a filter, for example, the bottom of a reservoir could be a filter disk, made of a suitable material, so that liquid reagents could be easily removed from a reservoir when desired.

Of the above substrate configurations all are potentially valuable in the present invention, since the only principle requirements for a suitable substrate are that the substrate be composed of a suitable solvent resistant material, as defined herein, and that one or more reservoirs exist in the substrate, which reservoir(s) open on a single surface of the substrate, and which reservoir(s) have at least a portion of an interior, inward facing surface thereof, activated for the attachment (or anchoring) of a protected carboxyl terminal amino acid thereto.

It is also envisioned herein, that one practicing the present invention, upon realizing the benefits associated with attaching peptides to reservoirs, (e.g., ease of interacting designed peptides with cells, etc.), may attach previously formed, but protected, peptides to interior, inward facing surfaces of reservoirs formed in suitable solvent resistant substrates. Particularly, since after attaching or anchoring a previously designed peptide to such a surface, one practicing the present invention could react the attached peptide with an unlimited multitude of reagents and materials, utilizing the automated methods taught herein.

Whether a peptide is built upon, or transferred to a surface of a reservoir, herein taught, it is fully expected that a peptide attached to such a reservoir surface would be useful in, but not limited to, the following: rapid screening and determination of B-cell and T-cell immunogenic protein sites, creation of synthetic vaccines, creation of synthetic diagnostic reagents, mapping virus-cell receptor sites, mapping of monoclonal antibody binding sites, determination of neutralization sites, localization of protein-cell receptor binding sites, stimulation of cells in response to active peptides derived from growth factors, neuropeptides, interleukins, selection of cell subsets responding to active peptides, and modelling of enzyme activity.

Once a suitable substrate, having a reservoir or reservoirs therein, has been selected, one desiring to practice the present invention must activate at least a portion of an interior, inward facing surface of each reservoir in the substrate, to which he ultimately desires to have attached a peptide. In the following discussion of means for activating suitable substrates, the substrate referred to is a microtiter plate, but the methods of activation herein taught are also applicable to the other suitable substrates herein taught.

In general, a suitable microtiter substrate must be chemically activated to provide a functional attachment site for the building thereon, or connecting thereto, of a peptide chain. For example, a suitable three-step means for introducing an amide functional group on a polyolefinic microtiter plate substrate would include oxidation, peroxidation, irradiation or polymer grafting of the polyolefinic substrate, to provide carboxyl groups thereon, and then reacting the carboxyl groups with a carbonyldiimidazole to give acyl imidazoles which are reacted with a suitable amine or polyamine, so that an amide is formed on the substrate surface.

It is noted that with the suitable substrates we have employed in our Examples herein (polyolefins), the functional groups which are produced on the substrate's surface during activation of the substrate is first a carboxyl group (i.e., —COOH) to which an amine (—$NH_2$) group is ultimately attached. But this should in no way be interpreted to limit the present invention, inasmuch as it is fully envisioned that other methods of producing functional groups, and even other functional groups could be used on the surface of a suitable substrate, to activate the same and allow for the ultimate attachment thereto of a peptide. For example, on a suitable glass substrate there can be introduced an amino containing molecule for the eventual attachment of a carboxy terminal amino acid, by silanization (e.g., by silanizing with amino-propyl-triethoxysilane) or by utilizing passive absorption techniques so that polymers are absorbed which contain appropriate functional groups.

Additionally, polymer grafting and copolymerization techniques can be utilized to provide activated substrates, wherein the functional group produced is either identical or different from those specifically provided herein. This is thought particularly true since the only real requirement for a suitable functional group is that it provide means for the anchoring or attachment of a carboxyl terminal amino acid chain to the chosen substrate. It should be considered that any of the above-discussed methods generally fall within the spirit and scope of the present invention.

Even though many different methods can be utilized to activate a suitable substrate, a simple and suitable method employs the oxidation of interior, inward facing surfaces of polyolefinic microtiter plate wells (e.g. TPX, Costar), or racks of polyolefinic tubes in a microtiter well format (commercially available from numerous vendors) with a suitable oxidizing acid, at a suitable temperature (such as nitric acid, at about 90–100° C., for about two hours) to produce carboxyl groups on the polyolefinic surfaces with which a carbonyldiimidazole and then a polyamine is reacted, in an appropriate solvent (e.g., N-methyl-2-pyrrolidone) to generate an amine functional group on the substrate for the eventual attachment of a peptide thereto. It is also noted that one may, if so desired, oxidize polyolefinic surfaces with nitric acid at room temperature, but the same is not believed preferred since formation of a suitable number of carboxyl groups on the polyolefinic substrate can take from several days to several weeks to occur.

Notwithstanding the above exemplary method, the use of other methods, or amine forming compounds (e.g., active ester intermediates), or even other oxidizing reagents, should be considered as being fully encompassed within the scope of the present invention, so long as the desired end is achieved (i.e., activation of the substrate for attachment of a peptide thereto).

It is noted that the functional group utilized to connect (or anchor) a peptide to a substrate's reservoir surface, must be resistant to chemical attack by those agents used to deprotect the α-amino group of the "protected carboxy terminal amino acids" herein employed, since of course, such a cleavable functional group should not cleave during deprotection of α-amino groups. It is also noted, however, that a suitable functional group could also be one that advantageously cleaves when desired, so that a formed peptide can separate from the substrate after, or before, completing scientific testing therewith or thereon, or when the same is to be used in a soluble form. It is emphasized that while the present invention provides for the use of cleavable functional groups for attaching peptides to a suitable substrate, the same should not be considered required in the methods provided herein.

Having activated a suitable substrate, so that functional sites exist thereon for the attachment of a protected carboxyl terminal amino acid thereto, the next step which must be performed, is the attachment of carboxyl terminal protected amino acid groups to such functional sites.

Before discussing the same, however, it is noted herein that novel solutions are provided which facilitate such an attachment step by allowing for the storage of solutions of amino acids for up to more than three (3) months, so that one desiring to practice the present invention, either manually or through the automated means herein provided, may advantageously avoid repetitive preparation of solutions of the twenty different amino acids generally used in peptide synthesis (and protected derivatives thereof) when peptide synthesis is performed. The preparation of such solutions are discussed below.

It has been found that by combining the following: (1) a protected carboxy terminal amino acid; and (2) an equimolar amount, or a slight excess (based on the amount of amino acid present) of either hydroxybenzotriazole, pentafluorohydroxyphenyl, or any other similar weakly acidic compound which can form an subsequent active ester with the amino acid, and which possess the ability to stabilize an FMOC protecting group, or the like, and protect it from removal by basic impurities generated within the solvents over time; in an appropriate organic solvent such as dimethylformamide, N-methyl-2-pyrrolidone, or the like, in which the derivative amino acids are freely soluble, and stable, and which can preferably solvate long peptide chains, that at a temperature of at most about −20° C. the same solutions have remained stable for up to more than three (3) months.

With regard to the above solutions, it was found in the present invention that while all of the above solutions remain stable, as desired, it appears that those solutions which contain N-methyl-2-pyrrolidone and hydroxybenzotriazole have led to increased efficiency in automated robotic cycles, when compared with those solutions containing dimethylformamide, and pentafluorophenol. For this reason, it is thought preferred to utilize storage solutions containing hydroxybenzotriazole and N-methyl-2-pyrrolidone if an automated synthesis of peptides is to be utilized.

Having formed any of the above stabilized solutions of carboxy terminal amino acids for later synthesis of peptides, an equimolar amount or a slight excess thereof (10–30%) of an appropriate condensing agent such as a carbodiimide (e.g., dicyclohexylcarbodiimide) must be added to the stabilized solutions before the solutions can be used to synthesize peptides. By adding an equimolar amount, or slight excess thereof, of such a condensing agent, active ester formation occurs in the previously stable solutions of the amino acids and weakly acidic compounds (such as hydroxybenzotriazole, pentafluorohydroxyphenyl, or the like). A suitable reaction solvent for the esterification is N-methyl-2-pyrrolidone, or the like. It is noted that after the activated amino acid esters are formed, such solutions will begin to degrade, but are usefully stable for at least 24 hours. It is noted that such a period of time (24 hours) is more than adequate for one skilled in the art to form peptide chains of about 20 (twenty) amino acid length, with the automated techniques taught herein.

Having discussed suitable substrates, activation of the same, and having provided stable solutions for storing amino acid solutions to be used in the peptide synthesis methods provided herein, we direct the attention of those desiring to practice the present invention to the synthesis of peptides, and even more particularly to the automated synthesis of peptides which utilize the substrates, and preferably the solutions disclosed above.

The following section details the procedure utilized herein to provide for automation of the peptide synthesis method provided herein. Specifically to the automated method thereof, and a flow chart representing the automated method. The method disclosed below for the automated synthesis of proteins can of course be performed manually if so desired, but with an expected loss in efficiency. Again, it is noted, that while the following discussion is limited to substrates having a "microtiter format", the same should not be considered limiting to the usefulness of other substrates disclosed herein in automated peptide synthesis. The following section concludes with Examples of peptide synthesis utilizing the automated methods herein provided.

Since the simultaneous synthesis of as many as 96 peptides, same or different, of lengths up to 21 or greater in a 96 well (or tube) microtiter plates (or rack), requires many thousands of pipetting, transfer, deblocking and washing steps, we sought to accomplish these steps robotically. The requisite characteristics of the robot, we determined should be (1) an ability to transfer solution from 20 activated amino acid solution containing reservoirs to the microtiter plate wells (or tubes), (2) an ability to deliver deblocking solution to microtiter wells/tubes, (3) an ability to deliver washing fluid and aspirate from microtiter wells/tubes, (4) adequate pipetting tools and transfer tips to accomplish the above, (5) and an ability to accept information related to the sequence of the desired peptides from external user-created files.

This is accomplished by using a Beckman Biomek 1000™ automated workstation, since the Beckman Biomek 1000™ workstation allows the use of externally created "pattern" files to designate which wells/tubes are to receive a transfer from a designated activated amino acid reservoir.

Before utilizing the Beckman Biomek 1000™, several changes were made to the same, these changes were necessitated as a result of the solvents used in peptide synthesis. For example, changes that were made included replacing or modifying certain solvent (NMP) sensitive components, including the following:

(1) the multi-bulk took O-rings were replaced with silicon O-rings;

(2) the multi-bulk tool purge tray was replaced with one of a similar configuration fabricated from polyethylene;

(3) the reservoir trays were replaced with reservoirs fabricated from polyethylene; and (4) silicone pump tubing was required and tubing in contact with the peristaltic pump rollers was wrapped with TEFLON tape.

With the Beckman Biomek 1000™, for each cycle a total of 20 patterns are needed, since the delivery of a single amino acid requires 1 pattern and 20 different amino acids can be delivered in a cycle.

Patterns need to be automated to automatically create the synthesis of linear overlapping peptides containing, in aggregate, the entire sequence information for any protein of a known sequence. Further sequence information is used to create patterns needed for the synthesis of arbitrary peptide sequences in desired wells or tubes.

Since the Beckman Biomek 1000™ only allows the use of 25 patterns at any given time, and 20 patterns are needed for each cycle, the robot is required to repetitively cycle through as many cycles and changes of pattern files as are needed to attain the desired peptide length. This is accomplished by utilizing the following method.

Figure 1:
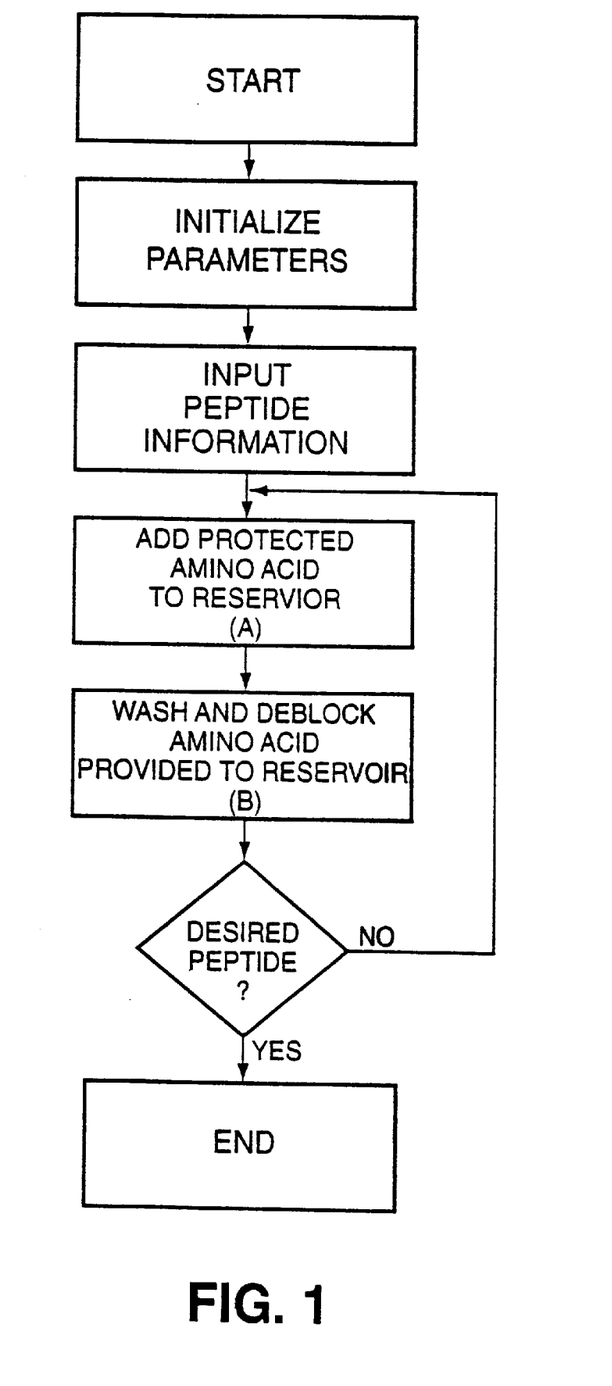
FIG. 1 illustrates the overall automated method used in the present invention.

FIG. 1 illustrates a flow chart showing the overall automated method utilized by the present invention in the automatic synthesizing of peptide sequences. Upon beginning the automated method, the present invention initializes various parameters to be utilized in the automated method. These parameters may include parameters directed to the name of the amino acids to be used and name of the peptide sequence to be created. Upon initializing the various parameters, the present invention receives inputted information concerning the peptide sequence to be created. This peptide sequence may be a known peptide sequence or an arbitrary peptide sequence. This allows the present invention to synthesize an arbitrary peptide sequence from a list of amino acids inputted by a user or to synthesize a known peptide sequence which has been previously stored in a file when a user indicates a desire to synthesize this known peptide sequence.

Notwithstanding, that in the accompanying drawings it is shown to proceed to the step of providing amino acids to the reservoirs after inputting peptide information, it is noted that one may optionally apply a washing and deblocking solution to the interior surfaces of reservoirs before the introduction into the reservoir of a first protected amino acid, and immediately hereafter aspirate the washing and deblocking solutions from the reservoir. It is generally felt that such a "pre-treatment" of the reservoir's interior surfaces may help to ensure that a consistent binding surface is present for the initial binding of an amino acid thereto.

After receiving the information concerning the desired peptide sequence, the present invention provides the first protected amino acid to be used in the synthesizing of the desired peptide sequence to the reservoir. The reservoir provides activated locations for the actual building (attachment) of the peptide sequence. A washing solution and deblocking solution is then provided to the reservoir to deblock the $\alpha$-amino groups of the just recently added and attached protected amino acid, and thereby creating a new point of attachment for a carboxyl terminal amino acid.

Upon completion of the washing and deblocking of the recently added amino acid, the present invention determines whether the synthesis of the desired peptide sequence has been achieved. If the synthesis of the desired peptide sequence has been achieved, the present invention terminates the automated method. On the other hand, if the synthesis of the desired peptide sequence is not complete, the automated method of the present invention repeats the adding of protected amino acids and the washing and deblocking amino acids steps until the desired peptide sequence is achieved.

Figure 2A:
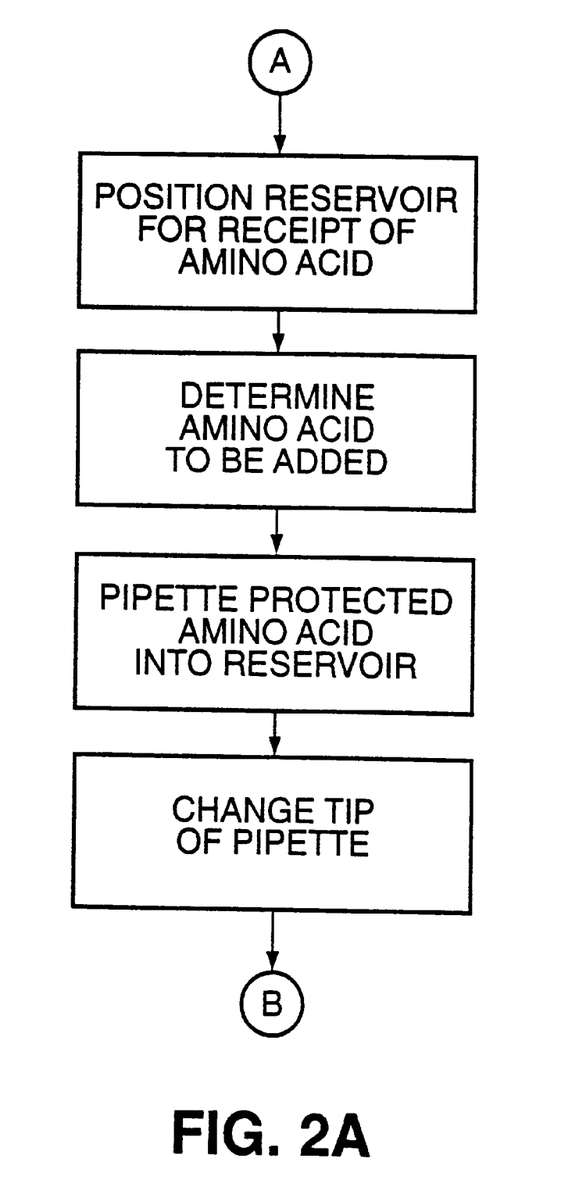
FIG. 2(A) illustrates a more detailed flowchart of the subroutine for adding a protected amino acid to the reservoir as represented by Block A in FIG. 1.

To achieve this desired automated method for the present invention, FIG. 2(A) illustrates a detailed flow chart of the step of FIG. 1 which adds the protected amino acid to the reservoir. In this addition step, the reservoir is initially positioned beneath a pipette to receive the protected amino acid. After positioning the reservoir properly under the pipette, the present invention determines from the sequence entered by the user or sequence previously stored, the protected amino acid to be added to the reservoir. This protected amino acid is then obtained by the present invention and pipetted into the reservoir. After the pipetting of the protected amino acid into the reservoir, the present invention changes the tip of the pipette in preparation of the addition of a different protected amino acid at a future time. The automated method of the present invention then proceeds to wash and deblock the protected amino acid previously provided to the reservoir.

Figure 2B:
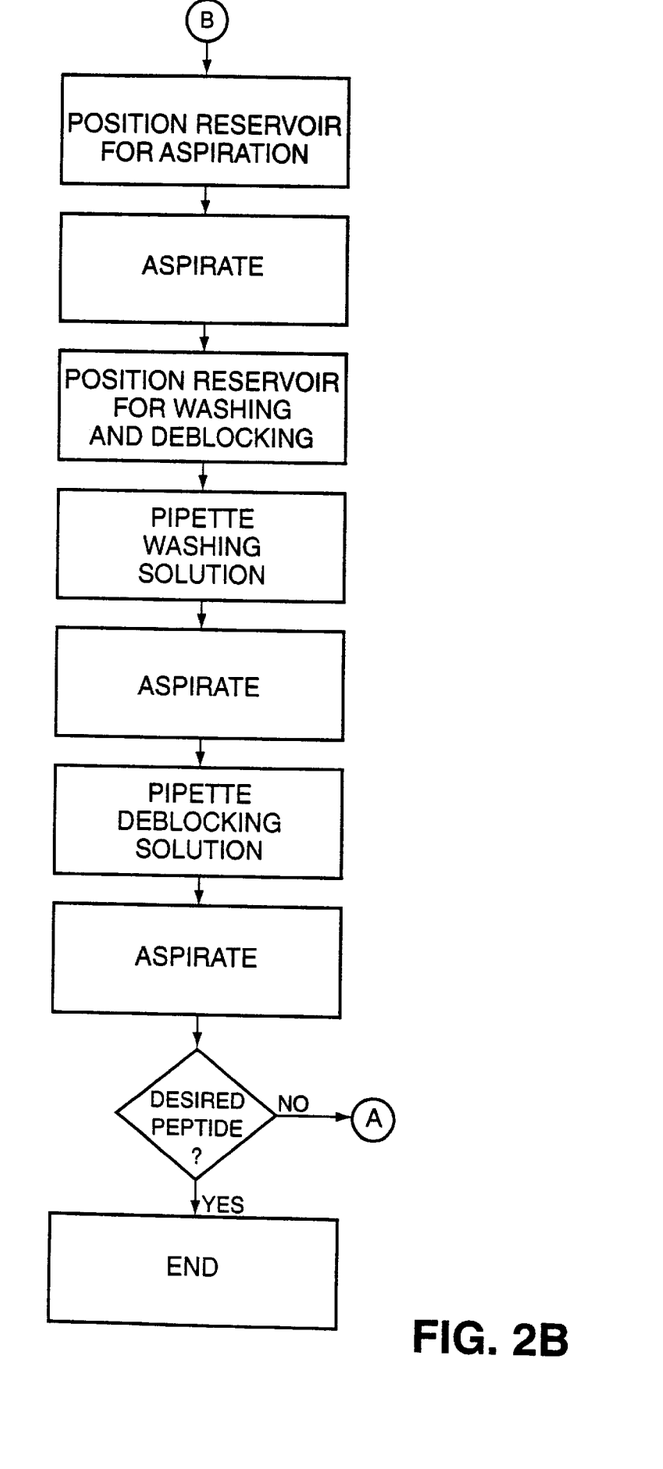
FIG. 2(B) illustrates a more detailed flow chart of the subroutine for washing and deblocking the protected amino acid provided to the reservoir as represented by Block B in FIG. 1.

FIG. 2(B) provides a detailed illustration of the step in FIG. 1 which washes and deblocks the protected amino acid provided to the reservoir. In this washing and deblocking step, the reservoir is initially positioned for aspiration. Upon obtaining the proper position, the reservoir is aspirated. In the preferred embodiment of the present invention, the aspiration step is accomplished the Beckman Biomek 1000™ multi-bulk tool, or a similar tool, which aspirates the reservoir fluid into an evacuated flask in approximately 1 minute. The step of aspiration is performed at ambient temperature. Even though the above aspiration method is preferred, the above aspiration method should not be construed to unduly limit the present invention, since other acceptable means for aspirating the reservoir could be used without departing from the scope of the present invention.

After aspiration, the reservoir is again positioned for washing and deblocking. After repositioning, the washing solution is pipetted in the reservoir. In a preferred embodiment of the present invention, the washing method preferably uses 1–4 washes of about 0.1 to 0.2 ml each of N-methyl-2-pyrrolidone, or the like, with aspiration after each wash.

Following aspiration of the washing solution, the present invention pipettes a deblocking solution into the reservoir. In a preferred embodiment of the present invention, the α-amino protecting group is an FMOC group and the same is removed by ammonolysis by utilizing a deblocking solution which comprises 20% (v/v) piperidine in N-methyl-2-pyrrolidone. It is noted that such a deblocking solution can deblock the FMOC protected α-amino groups, without cleaving the peptide from the substrate to which it is attached or removing side chain protecting groups on the amino acids which must be removed by acidolysis (e.g., a t-BOC group). Generally, from about 0.005 to 0.1 ml of solution is used in the deblocking step. The deblocking solution produces an unprotected α-amino group on the N-terminal amino acid. After the deblocking solution is pipetted into the reservoir, the reservoir is again aspirated. In the preferred embodiment of the present invention, the method for aspiration is performed as disclosed above, after a 5 minute incubation period wherein deblocking takes place.

At this point, the present invention determines whether the desired peptide has been achieved. If the desired peptide has been achieved, the automated method is terminated, whereas if the desired peptide has not been achieved, the automated method returns to the step for adding protected amino acids to the reservoir and repeats the steps illustrated in FIGS. 2(A) and 2(B) cyclically until the desired peptide is achieved.

Although the method has been described with respect to a single reservoir, a multiple number of reservoirs may be utilized simultaneously.

With respect to the above provided steps, it is noted that in the instance where one desires to utilize an α-amino blocking group such as t-BOC, or any similar blocking group, which must be removed by acidolysis with an acid such as trifluoroacetic acid, or some other similar acid, it then becomes necessary to pipet a neutralizing solution into the reservoirs after deblocking. After the acid has been neutralized with an acceptable basic substance such as a tertiary amine, the reservoir is aspirated. Such neutralizing and aspirating steps can be easily incorporated into the automated synthesis methods herein provided. For example, sequence instructions for patterns could be entered so that the neutralizing and aspirating steps are performed consecutively just after deblocking solution is pipeted into the reservoirs and then aspirated out of the reservoir(s) (See FIG. 2(B)). It is noted that in a preferred embodiment of the present invention, where FMOC groups are utilized to block α-amino groups of the amino acids, such additional neutralization and aspiration steps are not needed inasmuch as acidolysis is not required to remove FMOC blocking groups. A suitable solvent for removal of FMOC blocking groups by ammonolysis is as provided above, i.e., 20% (v/v) piperidine in N-methyl-2-pyrrolidone.

It is noted that after the above provided automated peptide synthesis method has been completed, and desired peptides formed, one may advantageously subject the peptides to several more treatment (or process) steps, which may or may not be automated. For example, side chain blocking groups may be removed with an appropriate solution. For example, when t-BOC blocking groups are used to block side chain amino groups on the amino acids, the same can be removed with a solution of 95% trifluoroacetic acid, 3% anisole, 1% ethanedithiol and 1% ethylmethylsulfide, or a similar solution. One may also, if desired, cleave the prepared peptides from the substrate surface, so that the same may be used in a soluble form, or so the same can be joined together so that longer proteins can be formed. Finally, if one so desires, the N-terminus of the peptide(s) can be modified, if desired, after the peptides are formed. Automated means for performing any of the above steps should be considered encompassed herein.

It is additionally envisioned that one using the techniques and methods herein employed for synthesizing peptides may find certain aspects of the same applicable to the automated synthesis of other organic molecules and macromolecules, such as sugars, or even strands of RNA and DNA.

The following Examples are included to more fully disclose certain aspects of the present invention and to aid those skilled in the art in practicing the present invention. The same should not be construed to limit the present invention, however, since the present invention is only limited by the scope of claims appended hereto.

EXAMPLE I

Methods

Preparation of Chemically Activated Surfaces

Figure 3:
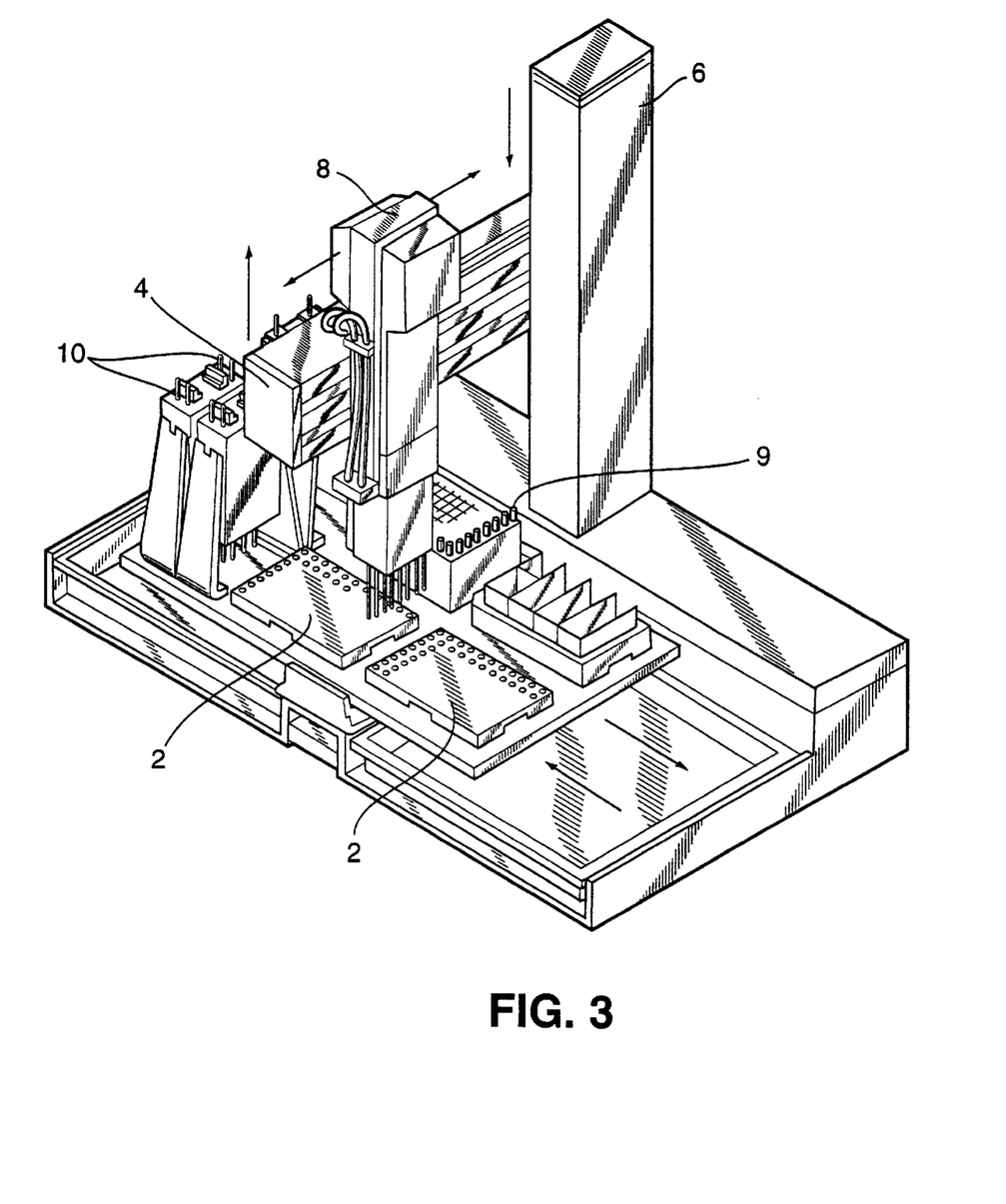
FIG. 3 is an illustration of the Beckman Biomek 1000™ workstation.

Costar TPX microtiter plate strip wells or polypropylene tubes in 96-well microtiter plate format were oxidized by contact with 70% nitric acid resulting in the formation of carboxyl groups on the surface. The extent of modification could be altered by adjusting the time, temperature or concentration of nitric acid. Reaction for two hours at 65° C., followed by rinsing with water was sufficient for the preparation of chemically activated surfaces. Alternatively, polyethylene, polypropylene, polyallomer could be used in place of polypropylene. Convenient fabrication forms for the Beckman Biomek 1000™ workstation were 96 well microtiter plates, 24 well microtiter plates, and clusters of tubes in microtiter format. As shown in FIG. 3, the Beckman Biomek 1000™ moves in three dimensions. The tablet (microtiter plate) 2 moves from left to right and right to left at the base of the workstation. The bridge 4 moves up and down the elevator tower 6. A specifically designed pod 8, which picks up the pipettes 9, photometry and other tools from the tool holders 10, moves forward and backward along the bridge 4. While alternative systems might easily be based on beads, rods, open flexible tubing, porous filters, etc., the value of using microtiter plates or clusters of tubes in a microtiter format was the existence of commercially available robotic workstations which could be used to automate the cyclical transfer of reagents in and out of reservoirs in a chosen substrate. An additional advantage of the microtiter plates and tubes was the opportunity to interact the peptides at the bottom of the well with cell surface receptors.

Conversion of Surface Carboxyl Function to Amine Function

Surface carboxyl groups were reacted with 0.05M carbonyl diimidazole in NMP for 30' at 20° C. Excess reagent was removed by aspiration and rinsed with methanol. Polyethyleneimine (1% in NMP) is reacted with the activated surface for 1 hour at 20° C.

Carboxyl could be suitably activated by many reagents such as carbodiimides or active ester intermediates. However, replacement of polyethyleneimine by poly-L-lysine or diaminoheptane or NMP by water resulted in decreased reactivity.

Preparation of Stock Solutions of FMOC-L-amino Acids 0.5M solutions of FMOC-L-amino acids were dissolved in NMP containing 0.5M HOBT. These solutions were stable for >3 months when stored at −20° C. Dimethylformamide or a similar solvent could be substituted for NMP.

Preparation of FMOC-L-amino Acid-HOBT Esters

Prior to peptide synthesis, the amount of each activated amino acid needed (depending of sequence composition and number of different peptides specified) was determined by computer program as the total number of additions to all wells over all cycles (doses). Solutions of 0.1M dicyclohexanecarbodiimide in NMP were first prepared for each amino acid. Next appropriate aliquots of (0.5M FMOC-L-amino acid+0.5M HOBT) in NMP were added so that all three reagents were in solution in equimolar amounts. The 20 mixtures were then allowed to react for 30' and then placed in a 24 tube rack in the Biomek workstation for use during the subsequent peptide synthesis cycles.

Peptide Synthesis Cycle

Each cycle began with an aspiration and 1 wash with NMP. FMOC (9-fluoroenyl-methoxycarbonyl) blocking groups were removed by reaction with 20% piperidine in NMP for 5 minutes, this was followed by 3 washes with NMP. Coupling and chain elongation was accomplished using 0.005M solutions of the FMOC-L-amino acid-HOBT esters in NMP for 25'. The total elapsed time for each synthesis cycle was 73'. After completion of the synthesis cycles blocking groups were removed with 95% trifluoroacetic acid containing 3% anisole, 1% ethanedithiol, 1% ethyl-methyl-sulfide. Under these conditions the peptides remained covalently bound to the plastic surface.

Peptide Synthesis

Microtiter plate wells/tubes were derivatized with polyethyleneimine as above. 0.5 ml Solutions of acid-labile or base-labile linkers (ALH, HALH, or BLH) were reacted with carbonyldiimidazole (1.0M each) for 30' at 20° C. The solution was then diluted to 5 cc with NMP and added to the wells/tubes and reacted for 1 hour at 20° C. The first amino acid was attached as the symmetrical amino acid anhydride after activation with DCC and addition of dimethylaminopyridine (DMAP). Thereafter, amino acids were attached as above. Completed peptides could be released with 95% TFA (ALH), 5% TFA (HALH), methanolic ammonia (BLH).

EXAMPLE II

Attachment of Previous Synthesized Peptides

Peptides synthesized via traditional preparative methods and linked to a support through a hyper-acid labile linker (HALH) may be released from their support with dilute TFA so that the peptide amino acid side chain blocking groups remain intact. The terminal carboxyl group may be activated via DCC and used directly or used to form activated esters (HOBT preferred) in DMF, NMP, methylene chloride, or mixtures of these. The activated peptide may then be reacted with the solvent resistant surfaces with functional amine groups (described above) to form a stable covalent bond with the surface. Side chain blocking groups may then be released as above.

The present invention is only to be limited by the appended claims.

What is claimed is:

1. A polyolefinic substrate which is solvent resistant and capable of forming —COOH groups upon oxidation with nitric acid, the substrate having one or more reservoirs therein, wherein each of said reservoirs opens on a single surface of said substrate, and wherein at least a portion of an interior, inward facing, surface of a reservoir therein has been activated for the anchoring of a protected carboxyl terminal amino acid thereto by reacting sequentially with (1) an acid capable of forming carboxyl groups on said interior surfaces of said reservoirs, (2) a carbonyldiimidazole, and (3) a polyamine.

2. The solvent resistant substrate of claim 1, wherein said substrate is in a microtiter format.

3. The solvent resistant substrate of claim 1, wherein the reservoir therein has been activated by reacting sequentially with (1) nitric acid at about 90–100° C. for about two hours, (2) a carbonyldiimidazole, and (3) a polyamine.

4. The solvent resistant substrate of claim 1, wherein the carbonyldiimidazole is N,N'-carbonyldiimidazole.

5. The solvent resistant substrate of claim 1, wherein the polyamine is polyethyleneimine or polypropyleneimine.

6. The solvent resistant substrate of claim 1, wherein the substrate comprises polyethylene, polypropylene or a polyallomer.

7. The solvent resistant substrate of claim 1, wherein the substrate comprises polyethylene, polypropylene, polymethylpentene or a polyallomer.

* * * * *